United States Patent [19]

van der Weerdt et al.

[11] Patent Number: 4,537,702

[45] Date of Patent: Aug. 27, 1985

[54] PERFUME AND FLAVORING COMPOSITIONS, PERFUMED ARTICLES AND MATERIALS, AND FLAVORED FOOD PRODUCTS CONTAINING AN OXASPIRODECADIENE DERIVATIVE AS THE ESSENTIAL COMPOUND, AS WELL AS THE OXASPIRO[4.5]DECADIENE DERIVATIVE PER SE

[75] Inventors: Antonius J. A. van der Weerdt, Huizen; Harrie Renes, Blaricum, both of Netherlands

[73] Assignee: Naarden International N.V., Naarden-Bussum, Netherlands

[21] Appl. No.: 493,412

[22] Filed: May 10, 1983

[30] Foreign Application Priority Data

May 13, 1982 [NL] Netherlands .......................... 8201991

[51] Int. Cl.$^3$ ...................... A61K 7/46; C07D 307/94
[52] U.S. Cl. ................................. 252/522 R; 426/536; 549/330
[58] Field of Search .................... 252/522 R; 549/330; 426/536

[56] References Cited

U.S. PATENT DOCUMENTS 3,890,395  6/1975  Jeger et al. ......................... 252/522 R
4,011,245  3/1977  Naegeli ............................. 252/522 R
4,014,905  3/1977  Skorianetz et al. ................. 252/522 R

FOREIGN PATENT DOCUMENTS 33959    8/1981  European Pat. Off. ........ 252/522 R
7214110  4/1973  Netherlands .
7601551  9/1976  Netherlands .
7608250  2/1977  Netherlands .
7809036  3/1979  Netherlands .
7711135  4/1979  Netherlands ..................... 252/522 R
2005138  4/1979  United Kingdom ............ 252/522 R

OTHER PUBLICATIONS

The Merck Index, 1976, Edition 9, pp. 972 and 973.

Primary Examiner—Anton H. Sutto
Attorney, Agent, or Firm—Brumbaugh, Graves, Donohue & Raymond

[57] ABSTRACT

Perfume and flavoring compositions, perfumed articles and materials respectively flavored foods, drugs, toothpaste, and tobacco products containing 10-isopropyl-2.7-dimethyl-oxaspiro[4.5]deca-3.6-diene having formula

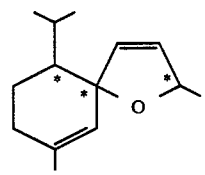

(I)

as essential compound for imparting thereto an olfactive note of the cassis type as well as this compound per se.

4 Claims, No Drawings

PERFUME AND FLAVORING COMPOSITIONS, PERFUMED ARTICLES AND MATERIALS, AND FLAVORED FOOD PRODUCTS CONTAINING AN OXASPIRODECADIENE DERIVATIVE AS THE ESSENTIAL COMPOUND, AS WELL AS THE OXASPIRO[4.5]DECADIENE DERIVATIVE PER SE

The invention relates to perfume and flavouring compositions containing a substituted oxaspiro[4.5]decadiene derivative as perfume respectively flavouring compound, to perfumed materials and articles respectively flavoured foods and allied products such as drugs, toothpaste, and tobacco containing this compound respectively compositions comprising this compound as well as to the substituted oxaspiro[4.5]decadiene derivative per se.

There is a continuous interest for the preparation and application of synthetic fragrances because these fragrances can always be prepared in the quantity desired and with uniform quality, this contrary to naturally occurring substances. Especially there is a demand for synthetic fragrances having a natural odour character.

Till now the characteristic odour of blackcurrants could hardly be used in a satisfying way. The odour in perfume compositions of compounds known in the flavour industry appeared to have too little of a specific blackcurrant character and the same comment may be applied to the blackcurrant-buds-absolue. Moreover many of these prior art flavouring components are sulphur compounds which find expression in their odour as a so-called sulphurous subnote, which, for perfumery, is undesired. Finally most of these basic compounds loose their blackcurrant-odour in alcoholic solution and for that reason these prior art compounds are not suitable for many perfume applications.

It was found that 10-isopropyl-2,7-dimethyl-1-oxaspiro[4.5]deca-3,6-diene having formula

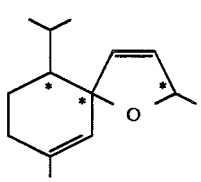

(I)

which compound has not been described earlier is a valuable and stable fragrance the odour of which has a very close resemblance with the characteristic odour of blackcurrants.

It is known of a number of mainly methyl substituted 1-oxaspiro[4.5]undecenes and -decadienes that these compounds may be used in perfume or flavouring compositions. For instance the perfume application of 2,6,9,10,10-pentamethyl-1-oxa-spiro[4.5]deca-3,6-diene having formula

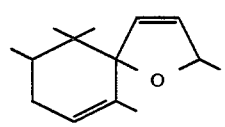

(2)

and the corresponding 2,6,9,10- and 2,6,7,10-tetramethyl compounds having formulae

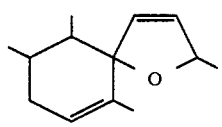

(3)

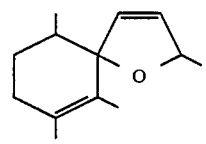

(4)

as described in respectively the published Dutch patent application Nos. 76,08250 and 77,11135. Although these compounds have besides a green odour reminding of mint leaves and sauge sclaree also a somewhat blackcurrant-like note they do not show that characteristic only of blackcurrants reminding odour which is necessary to impart a blackcurrant-nuance to perfume compositions.

In the published Dutch patent application No. 76,01551 it is disclosed that 2,6,10,10-tetramethyl-1-oxaspira[4.5]dec-6-ene having formula

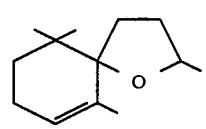

(5)

has a fresh-fruity odour with a currant-like green note. However, also this compound misses the specific odour of blackcurrants.

A number of 6-methylene-trimethyl- and -tetramethyloxaspirodecenes and -decadienes having formula

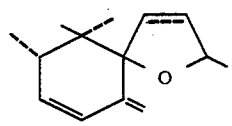

(6)

has been described in the published Dutch patent application No. 78,09036. These compounds are characterized by a camphoric woody and earthy odour with in some cases a fruity note reminding of apples or plums.

In Dutch patent application No. 72,14110 it is described that a number of 6-methylene-oxaspirodecanes having formula

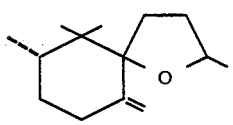

(7)

have an odour reminding of parmavioles. The compounds described in this patent application lack any blackcurrant-character. Finally 6-ethyl-2,10,10-trimethyl-1-oxaspiro[4.5]deca-3,6-diene having formula

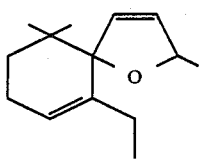

has been described in the European patent application No. 33,959 as a compound having an odour clearly reminding of blackcurrants. As appears from the above indicated formulae 2 up to 8 all these compounds according to the known prior art have a highly corresponding substitution pattern in the cyclohexene ring characterized by:

1. at least 2 but mostly 3 substituents at the α-position with respect to the spiro-atom;
2. the substituents are all methyl(ene) groups with as the only exception the ethyl group in the compound having formula 8.

The compounds having the formulae 2, 5, 6, 7 and 8 are either found in natural products like: tea, tobacco, passion fruit and osmanthus blossom or are strongly related with compounds found therein.

Therefore it is the more remarkable that the compound according to the invention characterized by a substitution pattern which completely deviates from that of the above mentioned compounds has a so strong and qualitively excellent odour of blackcurrant-buds absolue which surpasses yet in natural fulness the odour of the compound having formula 8.

The compound according to the invention is also very suitable for flavouring of foods and allied products. The compound is characterized by a fruity somewhat woody taste strongly reminding of blackcurrant juice. It can be used advantageously for the preparation of flavouring compositions for instance fruit flavourings like blackcurrant flavourings, raspberry flavourings and other berry-like flavourings.

The compound according to the invention can be prepared according to methods known per se for analogous compounds for instance as described in the above mentioned Dutch patent application Nos. 77,11135 and 76,08250 and the European patent application No. 33,959. In this respect the present compound has the advantage that for the synthesis thereof the easy and cheap obtainable starting compound piperitone can be used; vide the undermentioned reaction equation:

FIG. 2

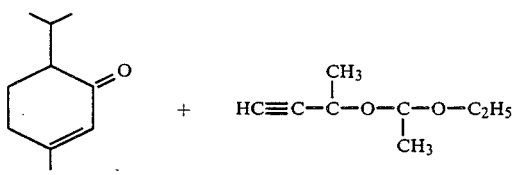

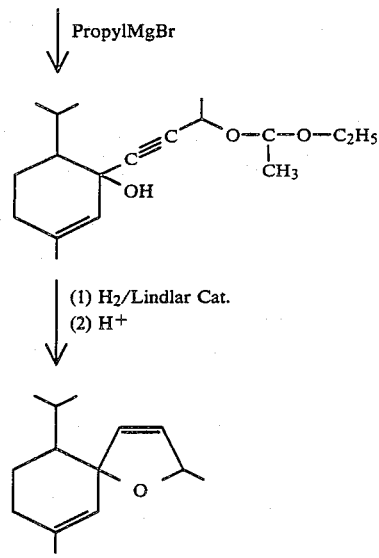

On the other hand for preparing the compound having formula 8 according to the above mentioned European patent application one should dispose of the relatively difficult obtainable starting compound 2-ethyl-6,6-dimethyl-cyclohexanone.

The compound according to the invention has three asymetric carbon atoms which are indicated in formula 1 with the symbol *. The invention relates to the different stereo-isomers individually as well as mixtures thereof. Generally a mixture of stereo-isomers is obtained by the synthesis. The stereo chemistry with respect to the asymetric carbon atom (10) can easily be influenced by starting the synthesis with D- or L-piperitone. However, the organoleptic differences between both stereo-isomers obtained therefrom are small. For practical and economic reasons the mixture of isomers obtained by the synthesis is used as such as perfume and flavouring compound.

When applied as a perfume compound the present compound can be used as such as odour imparting agent as well as successfully in all kinds of perfume compositions in which an odour aspect of blackcurrants is desired.

The phrase "perfume composition" is used to mean a mixture of fragrances and optionally auxiliary substances that may be dissolved in an appropriate solvent or mixed with a powdery substrate and used to impart a desired odour to the skin and/or various products. Examples of such products are: soaps, detergents, air-refreshers, roomsprays, pommanders, candles, cosmetics like creams, ointments, colognes, pre- and after-shave lotions, talcum powders, haircare agents, body deodorants and antiperspirants.

Fragrances and mixtures thereof which in combination with the compound according to the invention can be used for the preparation of perfume compositions include for instance: natural products such as essential oils, absolutes, resinoids, resins, concretes, etc., but also synthetic fragrances, such as hydrocarbons, alcohols, aldehydes, ketones, ethers, acids, esters, acetals, ketals, nitriles etc., both saturated and unsaturated compounds, aliphatic, carbocyclic and heterocyclic compounds.

Examples of fragrances to be used in combination with the compound according to the invention include geraniol, geranyl acetate, linalool, linalyl acetate, tetrahydrolinalool, citronellol, citronellyl acetate, myrcenol, myrcenyl acetate, dihydro myrcenol, dihydro myrcenyl acetate, tetrahydro myrcenol, terpineol, terpinyl acetate, nopol, nopyl acetate, β-phenyl ethanol, β-phenylethyl acetate, benzyl alcohol, benzyl acetate, benzyl salicylate, benzyl benzoate, amyl salicylate, styrallyl acetate, dimethylbenzyl carbinol, trichloromethylphenylcarbinyl acetate, p-tert.butyl cyclohexyl acetate, isononyl acetate, vetiveryl acetate, vetiverol, α-hexyl cinnamaldehyde, 2-methyl-3-(p-tert.butylphenyl)-propanal, 2-methyl-3(p-isopropylphenyl)-propanal, 2-methyl-3-(p-tert.butylphenyl)-propanal, tricyclodecenyl acetate, tricyclodecenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyl-tetrahydro pyran, 3-carboxymethyl-2-pentylcyclopentane, 2-n-heptyl cyclopentanone, 3-methyl-2-pentyl-2-cyclopentanone, n-decanal, n-dodecanal, 9-decenol-1, phenoxyethyl isobutyrate, phenyl acetaldehyde dimethylacetal, phenyl acetaldehyde diethylacetal, geranyl nitrile, citronellyl nitrile, cedryl acetate, 3-isocamphyl cyclohexanol, cedrylmethyl ether, isolongifolanon, aubepine nitrile, aubepine, heliotropine, coumarin, eugenol, vanillin, diphenyl oxide, hydroxy citronellal, ionones, methyl ionones, isomethyl ionones, irones, cis-3-hexenol and esters thereof, indan musk fragrances, tetralin musk fragrances, isochroman musk fragrances, macrocyclic ketones, macrolactone musk fragrances, ethylene brassylate, and aromatic nitromusk fragrances.

Auxiliary agents and solvents that may be incorporated into perfume compositions according to the invention comprise for example ethanol, isopropanol, diethylene glycol monoethylether, and diethyl phtalate.

The amount of the compound of the invention that can be used in perfume compositions or in perfumed products can be varied within broad limits and depends for example on the product wherein the perfume is used, the nature and the amount of the further components of the perfume compositions and the odour effect desired. Therefore, it is only possible to indicate very rough limits. However, these limits will give a person skilled in the art sufficient information concerning the odour strength and possibilities for the use of the compounds according to the invention. In most cases a quantity of only 0.02% by weight in a perfume composition is sufficient to obtain a clearly observable odour effect. In some cases, however, concentrations of 30% by weight may be used in the compositions for obtaining special odour effects.

In products perfumed with the aid of perfume compositions according to the invention the concentration of the instant compound is proportionally lower and depends on the quantity of the composition used in the product.

When used as flavouring compound the compound according to the invention may be used advantageously in an amount of 0.01-100 ppm in the flavoured foods and allied products.

The phrase "foods and allied products" includes solid and liquid products intended for human consumption also comprising tobacco products, drugs and tooth paste.

The following examples only illustrate the preparation and use of the compound according to the invention and do not restrict the invention thereto.

EXAMPLE I

Preparation of 10-isopropyl-2,7-dimethyl-1-oxaspiro[4.5]deca-3,6-diene

A.                                                                      FIG. 1

$$HC\equiv C-\underset{OH}{\underset{|}{C}}-CH_3 + H_2C=CH-O-C_2H_5 \longrightarrow$$

$$HC\equiv C-\underset{CH_3}{\underset{|}{C}}-O-\underset{CH_3}{\underset{|}{C}}-O-C_2H_5$$

765 g ethylvinylether was cooled down to about −10° C. whereafter 1 g thionylchloride and then in 1 hour 720 g but-1-yn-3-ol were added. The mixture was stirred 1 hour at −5° C. and then another hour at 45° C. After adding of 5 g triethanol the mixture was distilled in vacuo.

Yield: 1187 g 3,5-dimethyl-4,6-dioxa-oct-1-yn.
Boiling point: 80° C./12 kPa.

B.                                                                      FIG. 2

[structural diagram: piperitone + HC≡C−C(CH₃)(OC(CH₃)OC₂H₅)]

↓ PropylMgBr

[structural diagram: cyclohexenyl intermediate with alkyne and OH]

(1) H₂/Lindlar Cat.
(2) H⁺

↓

[structural diagram: 10-isopropyl-2,7-dimethyl-1-oxaspiro[4.5]deca-3,6-diene]

A solution of 1-propylmagnesium bromide was prepared from 120 g magnesium and 610 g 1-bromopropane in 5 l tetrahydrofuran. To this solution 710 g of the above mentioned dioxa-octyne was added 1 hour whereby the temperature of the reaction mixture raised to about 60° C. and propane evaporated. The reaction mixture was stirred another hour during which the temperature dropped to 30° C. Then in 1 hour 700 g freshly distilled piperitone was added and the mixture was stirred 1 hour at 60° C. After cooling off the reaction mixture was poured out in a mixture consisting of 1000 g ammonium chloride and 5000 g ice/water and stirred thoroughly. The layers were separated and the organic layer was washed 3 times with water and dried above Na$_2$SO$_4$. The solution was evaporated in vacuo and subsequently the unreacted starting material was distilled off in vacuo (max. 85° C. at 0.2 kPa). Yield: 1100 g dioxy-octynyl-cyclohexenol-derivative.

C. (Vide the above figure indicated under (B)

480 g of the last mentioned reaction product was dissolved in 350 ml methanol after which 2.5 g Lindlar-catalyst was added. This mixture was hydrogenated at 40° C. and 400 kPa until no more hydrogen was taken up. Then the catalyst was filtrated off and the solvent was evaporated in vacuo. To the residue 500 g 30%'s sulphuric acid was added. This mixture was stirred during 2 hours at 20° C. and subsequently 2 hours at 40° C. Then the layers were separated and the organic layer was washed twice with a soda-solution. Further the organic layer was distilled and fractionated both steps in vacuo.

Yield: 200 g (60%) 10-isopropyl-2,7-dimethyl-1-oxaspiro[4.5]deca-3,6-diene.

Boiling point: 83°–85° C./0.2 kPa; $n_D$=1.4918.

EXAMPLE II

A perfume composition for soap was prepared according to the following recipe:

| | |
|---|---|
| 160 | parts by weight of 4-tert.butyl-cyclohexyl acetate |
| 160 | parts by weight of benzylsalicylate |
| 110 | parts by weight of terpinylacetate |
| 110 | parts by weight of nopyl acetate |
| 60 | parts by weight of phenylethyl-amylether |
| 60 | parts by weight of hydroxycitronellal |
| 60 | parts by weight of benzyl acetate |
| 50 | parts by weight of 6-acetyl-1-isopropyl-2,3,3,5-tetramethyl-indan |
| 50 | parts by weight of gamma-methyljonon |
| 30 | parts by weight of phenylethanol |
| 30 | parts by weight of ylang oil |
| 30 | parts by weight of alpha-n.amyl cinnamaldehyde |
| 15 | parts by weight of cumarin |
| 15 | parts by weight of musk ambrette |
| 15 | parts by weight of alpha-jonon |
| 10 | parts by weight of guajak wood oil |
| 5 | parts by weight of undecen-10-al |
| 5 | parts by weight of 2-methyl-3-(p-isopropylphenyl)-propanol |
| 25 | parts by weight of 10-isopropyl-2,7-dimethyl-1-oxaspiro[4.5]deca-3,6-diene |
| 1000 | parts by weight |

A perfumed toilet soap was prepared by thoroughly mixing of 1 kg white soap granules, 10 g of the above mentioned perfume composition and 10 g of a soap dye in a pilling machine. The obtained perfume coloured soap flakes were pressed in a usual way to pieces of toilet soap. In this way a pleasently smelling toilet soap was obtained having a light but stable cassis-note.

EXAMPLE III

A perfume composition for an aftershave lotion was prepared according to the following recipe:

| | |
|---|---|
| 240 | parts by weight of bergamot oil, bergaptene-free |
| 80 | parts by weight of vetiveryl acetate |
| 80 | parts by weight of n.amylcinnamaldehyde |
| 80 | parts by weight of cedar wood oil |
| 80 | parts by weight of lemon oil, Italian |
| 80 | parts by weight of orange oil, Florida |
| 80 | parts by weight of benzyl acetate |
| 30 | parts by weight of 6-acetyl-1-isopropyl-2,3,3,5-tetramethyl-indan |
| 30 | parts by weight of methyl-dihydrojasmonate |
| 30 | parts by weight of cis-hex-3-en-1-ylsalicylate |
| 30 | parts by weight of 2-methyl-3-(p-isopropylphenyl)-propanol |
| 20 | parts by weight of musk ambrette |
| 20 | parts by weight of galbanum resinoid |
| 20 | parts by weight of styrallyl acetate |
| 15 | parts by weight of oil of cloves |
| 10 | parts by weight of heliotropine |
| 10 | parts by weight of cumarin |
| 10 | parts by weight of 11-oxahexadecanolide |
| 10 | parts by weight of armoise oil |
| 10 | parts by weight of 2-methyl-3-(3,4-dioxymethylene-phenyl)-propanal |
| 35 | parts by weight of 10-isopropyl-2,7-dimethyl-1-oxaspiro[4.5]deca-3,6-diene |
| 1000 | parts by weight |

EXAMPLE IV

An aftershave lotion perfumed with a composition according to example III was prepared according to the following recipe:

A.
 0.3 part by weight of 1-menthol
 0.5 part by weight of uvinol D 50[1]
 30.0 parts by weight of propylene glycol
 535 parts by weight of ethanol B.
 2.0 parts by weight of aluminum-chlorohydrate-allantoinate
 2.0 parts by weight of lactic acid
 400 parts by weight of water (distilled)

C.
 20 parts by weight of perfume (example III)
 10 parts by weight of cremophor RH40[2]

[1]Trade mark of BASF for 2,2',4,4'-tetrahydroxybenzophenone.
[2]Trade mark of BASF for the reaction product of hydrogenated castor oil and epoxyethane.

The components mentioned under A, B and C were mixed separately to the mixtures A, B and C. Mixture B was then added to mixture A under thoroughly stirring. Then mixture C was added and the total mixture was homogenized by stirring. In this way a somewhat astringating aftershave-lotion was obtained which gave a pleasant odour with a light but stable cassis note.

EXAMPLE V

A blackcurrant flavouring was prepared according to the recipe of Fenaroli's Handbook of Flavor Ingredients, Volume II, 2nd Edition (1975), page 586, (CRC Press, Cleveland, Ohio). To this flavouring one part by weight of 10-isopropyl-2,7-dimethyl-1-oxaspiro[4.5-]deca-3,6-diene was added per 1000 parts by weight of flavouring. The flavouring obtained by this addition became a more fully and natural blackcurrant character than the flavouring without this addition.

We claim:
1. Perfume and flavoring compositions, perfumed articles and materials, and flavoured food products containing an oxa-spirodecadiene derivative as the basic compound, characterized by a content of 10-isopropyl-2,7-dimethyl-1-oxaspiro[4.5]deca-3,6-diene as the oxa-spirodecadiene derivative.

2. A perfume composition according to claim 1, characterized by a content of at least 0.02% by weight of 10-isopropyl-2,7-dimethyl-1-oxaspiro[4.5]deca-3,6-diene.

3. Flavoured foods, characterized by a content of 0.01–100 ppm of 10-isopropyl-2,7-dimethyl-1-oxaspiro[4.5]deca-3,6-diene.

4. 10-Isopropyl-2,7-dimethyl-1-oxaspiro[4.5]deca-3,6-diene.

* * * * *